United States Patent [19]
Mensa-Wilmot

[11] Patent Number: 5,874,242
[45] Date of Patent: Feb. 23, 1999

[54] EFFICIENT TRANSLATION IN EUKARYOTIC AND PROKARYOTIC SYSTEMS

[75] Inventor: Kojo A. Mensa-Wilmot, Athens, Ga.

[73] Assignee: University of Georgia Research Foundation, Inc., Athens, Ga.

[21] Appl. No.: 821,022

[22] Filed: Mar. 19, 1997

[51] Int. Cl.$^6$ .......................... C12P 21/02; C12N 15/63; C12N 15/11

[52] U.S. Cl. .................. 435/69.1; 435/172.3; 435/252.3; 435/252.33; 435/320.1; 435/325; 435/410; 536/23.1; 536/24.1

[58] Field of Search ................................ 435/69.1, 320.1, 435/172.3, 252.3, 252.33, 325, 410; 536/24.1, 23.1

[56] References Cited

PUBLICATIONS

He et al. Phage RNA polymerase vectors that allow efficient gene expression in both prokaryotic and eukaryotic cells. Gene vol. 164 pp. 75–79, 1995.

Margolskee et al. Epstein–Barr virus shittle vector for stabe episomal replication of cDNA expression libraries in human cells. Molecular and Cellular Biology vol. 8 pp. 2837–2847, 1988.

Al–Qahtani, A. et al. (1996) "A 5' untranslated region which directs accurate and robust translation by prokaryotic and mammalian ribosomes," Nucleic Acids Research 24(6):1173–1174.

Buell, G. et al. (1985) "Optimizing the expression in *E. coli* of a synthetic gene encoding somatomedin–C (IGF–I)," Nucleic Acids Research 13(6):1923–1938.

Derman, et al. (1993) "A signal sequence is not required for protein export in *prlA* mutants of *Escherichia coli*," The EMBO Journal 12(3):879–888.

Gray, G. et al. (1984) "Synthesis of bovine growth hormone by *Streptomyces lividans*," Gene 32:21–30.

Hereld, D. et al. (1988) "cDNA encoding the glycosyl–phosphatidylinositol–specific phospholipase C of *Trypanosoma brucei*," Proc.Natl.Acad.Sci.USA 85:8914–8918.

Kozak, M. (1994) "Determinants of translational fidelity and efficiency in vertebrate mRNAs," Biochimie 76:815–821.

Kozak, M. (1995) "Features in the 5' Non–coding Sequences of Rabbit α and β–Globin mRNAs that Affect Translational Efficiency," J. Mol. Biol. 235:95–110.

Kozak, M. (1987) "At Least Six Nucleotides Preceding the AUG Initiator Codon Enhance Translation in Mammalian Cells," J. Mol. Biol. 196:947–950.

LeBowitz, J.H. et al. (1993) "Coupling of poly(a) site selection and trans–splicing in *Leishmania*," Genes & Development 7:996–1007.

Mensa–Wilmot, K. et al. (1990) "Genomic Organization, Chromosomal Localization, and Developmentally Regulated Expression of the Glycosyl–Phosphatidylinositol–Specific Phospholipase C of *Trypanosoma brucei*," Molecular and Cellular Biology 10(2):720–726.

Mensa–Wilmot, K. et al. (1992) "Glycosyl phosphatidylinositol–specific phospholipase C of *Trpanosoma brucei*: expression in *Escherichia coli*," Molecular and Biochemical Parasitology 56:311–322.

Mensa–Wilmot, K. et al. (1994) "A Glycosylphosphatidylinositol (GPI)–Negative Phenotype Produced In *Leishmania major* by GPI Phospholipase C from *Trypanosoma brucei*: Topography of Two GPI Pathways," The Journal of Cell Biology 124(6):935–947.

Mensa–Wilmot, K, et al. (1995) "Purification and Use of Recombinant Glycosylphosphatidylinositol–Phospholipase C," Methods in Enzymology 250(46):654–655.

Mensa–Wilmot, K. et al. (1992) "Non–fusion proteins expressed in *E. coli*: detection by α–complementation (blue/white selection)," Nucleic Acids Research 20(1):143.

*Primary Examiner*—John L. LeGuyader
*Assistant Examiner*—John S. Brusca
*Attorney, Agent, or Firm*—Greenlee, Winner and Sullivan, PC

[57] ABSTRACT

The present disclosure provides sequences and methods for efficient protein synthesis in eukaryotic and prokaryotic host cells.

6 Claims, 6 Drawing Sheets

```
                                          Msp I
                                          Rsa I
               Mse I                      Csp6 I
           Sau3A I                        Nla IV
           Mbo I                          Kpn I
           Dpn II                         Ban I
           Dpn I                          Acc65 I
           Alw I                       Nla III
           Nla IV                      Sty I    BsrF I
           BstY I                      Nco I    BsaW I
           BamH I                      Dsa I    Age I
           Alw I              Mnl I    BsaJ I   Hpa II
           | |                 |       | |  | | | |
         TAAGGATCCTTAACACAGGAGGCAGACCATGGTACCGGT   39
         ATTCCTAGGAATTGTGTCCTCCGTCTGGTACCATGGCCA
           | |                 | •     | | •| | | |
           4                   19      27        35
           4                           27        34
           4                           27        34
           4                           27        34
            5                           28
            5                              31
            5                              31
            5                              31
            5                              31
                   10                         32
                                              32
                                                 35
```

FIG. 2A

```
1  TAAGGATCCTTAACACAGGAGGCAGACC ATG GTA CCG GT   39
1                                M   V   P       3
```

FIG. 2B

```
            Mse I
     Sau3A I
     Mbo I
      Dpn II
      Dpn I
      Alw I                          Msp I
      Nla IV                         Hpa II
      BstY I                         BsrF I
      BamH I                         BsaW I
      Alw I            Mnl I         Age I
      | |    |           |            | |
   TAAGGATCCTTAACACAGGAGGCAGACGggt      31
   ATTCCTAGGAATTGTGTCCTCCGTCTGGcca
      | |    |           | •          | |  •
      4                 19            26
      4                               26
      4                               26
      4                               27
       5                              27
       5
       5
       5
       5
            10
```

FIG. 3

```
              Mse I
       Sau3A I
        Mbo I
        Dpn II
        Dpn I
        Alw I
       Nla IV
       BstY I
       BamH I
        Alw I            Mnl I      Nde I
        | |    |           |          |
       TAAGGATCCTTAACACAGGAGGCAGACCatatg    33
       ATTCCTAGGAATTGTGTCCTCCGTCTGGtatac
        | |    |           |•         |•
        4                 19         28
        4
        4
        4
         5
         5
         5
         5
         5
              10
```

FIG. 4

```
            Mse I
      Sau3A I
      Mbo I
      Dpn II
      Dpn I
      Alw I
      Nla IV                          Ppu10 I
      BstY I                          Nsi I
      BamH I              BspW I
      Alw I               Mnl I    Nla III
      | |    |            |   |    | |
     TAAGGATCCTTAACACAGGAGGCAGAccatgcat    34
     ATTCCTAGGAATTGTGTCCTCCGTCTggtacgta
      | |    |            | • |    | |•
      4                   19       28
      4                   22
      4                            29
      4                            29
       5
       5
       5
       5
       5
            10
```

FIG. 5

```
            Mse I
      Sau3A I
      Mbo I
      Dpn II
      Dpn I
      Alw I              Nla III
     Nla IV              Sty I
     BstY I              Nco I
     BamH I              Dsa I
      Alw I      Mnl I   BsaJ I
     | |   |      |      | |
 TAAGGATCCTTAACACAGGAGGCAGAccatgg    32
 ATTCCTAGGAATTGTGTCCTCCGTCTggtacc
     | |   |      | •    | | •
      4           19      27
      4                   27
      4                   27
      4                   27
       5                  28
       5
       5
       5
       5
            10
```

FIG. 6

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO:1:

A G G A G G G T T T  T T A    1 3

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO:2:

A G G A G G G T T T  T T A C C    1 5

( 2 ) INFORMATION FOR SEQ ID NO:3:

( i ) SEQUENCE CHARACTERISTICS:
    ( A ) LENGTH: 56 base pairs
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO:3:

TAAGGATCCT TAACTTAGGA GGGTTTTTAC CATGACACCA GAAATGCCTG TTCTGG      56

( 2 ) INFORMATION FOR SEQ ID NO:4:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO:4:

GATCGGATCC TTAAGATCTG CCCCAGAGCG GCTTTCATGG      40

( 2 ) INFORMATION FOR SEQ ID NO:5:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO:5:

TAAGGATCCT TAACACAGGA GGGTTTTTAC CATGTTTGGT GGT      43

( 2 ) INFORMATION FOR SEQ ID NO:6:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO:6:

TATGTGGATC CTTATGACCT TGCGGTTTGG TT      32

( 2 ) INFORMATION FOR SEQ ID NO:7:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: NO (x i) SEQUENCE DESCRIPTION: SEQ ID NO:7:

AGGAGGCAGA CC                                                                                    12

(2) INFORMATION FOR SEQ ID NO:8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: other nucleic acid (i i i) HYPOTHETICAL: NO (x i) SEQUENCE DESCRIPTION: SEQ ID NO:8:

AGGAGGCAGA TC                                                                                    12

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: other nucleic acid (i i i) HYPOTHETICAL: NO (x i) SEQUENCE DESCRIPTION: SEQ ID NO:9:

AGGAGGGTTT TTATC                                                                                 15

(2) INFORMATION FOR SEQ ID NO:10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (i i) MOLECULE TYPE: other nucleic acid (i i i) HYPOTHETICAL: NO (x i) SEQUENCE DESCRIPTION: SEQ ID NO:10:

TAAGGATCCT TAACACAGGA GGCAGACCAT GGTACCGGT                                                        39

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (i i) MOLECULE TYPE: other nucleic acid (i i i) HYPOTHETICAL: NO (x i) SEQUENCE DESCRIPTION: SEQ ID NO:11:

TAAGGATCCT TAACACAGGA GGCAGACCGG T                                                                31

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO:12:

TAAGGATCCT TAACACAGGA GGCAGACCAT ATG 33

( 2 ) INFORMATION FOR SEQ ID NO:13:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO:13:

TAAGGATCCT TAACACAGGA GGCAGACCAT GCAT 34

( 2 ) INFORMATION FOR SEQ ID NO:14:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO:14:

TAAGGATCCT TAACACAGGA GGCAGACCAT GG 32

( 2 ) INFORMATION FOR SEQ ID NO:15:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO:15:

GCCGCCRCCA UGG 13

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: Not Relevant ( i i ) MOLECULE TYPE: other nucleic acid
        ( A ) DESCRIPTION: /desc = "Oligonucleotide."

( i i i ) HYPOTHETICAL: NO ( x i ) SEQUENCE DESCRIPTION: SEQ ID NO:16:

AGGAGGGTTT TTACCATG 18

(2) INFORMATION FOR SEQ ID NO:17:

(i) SEQUENCE CHARACTERISTICS:
        (A) LENGTH: 15 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:17:

AGGAGGCAGC TAATG          15

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:18:

GTTAAGAATC ATTGTAATG          19

EFFICIENT TRANSLATION IN EUKARYOTIC AND PROKARYOTIC SYSTEMS

ACKNOWLEDGEMENT OF FEDERAL RESEARCH SUPPORT

This invention was made, at least in part, with funding from the National Institutes of Health (Grant No. 29 AI33383). Accordingly, the United States Government may have certain rights in this invention.

THE BACKGROUND OF THE INVENTION

There is a longfelt need in the art for expression vectors which enable efficient expression both in a prokaryotic host organism of choice, preferably *Escherichia coli*, as well as in eukaryotic recombinant host organisms, protozoans, plant cells, yeast cells and mammalian cells including but not limited to, COS cells.

SUMMARY OF THE INVENTION

It is an object of the present invention to provide compositions and methods for the efficient translational expression of coding sequences in recombinant eukaryotic host cells as well as in recombinant prokaryotic host cells. This can be accomplished by the use of expression vectors in which the nucleotides immediately upstream of the translational start codon are GCC, ATC or ACC; preferably a sequence selected from the group consisting of SEQ ID NO:7, SEQ ID NO:8, SEQ ID NO:9 and SEQ ID NO:10. As used herein, these sequences are termed "universal translation enhancement sequences." In such an expression vector, there is an origin of replication which is functional in the recombinant host cell of choice, and in the case where it is desired that the vector replicate in more than one host cell, there are replication origins present in the vector which are functional in the desired host cell types. The transcriptional expression of the desired coding sequence is accomplished by the incorporation of transcriptional control signals (promoter and optionally further including transcription-enhancing sequences) upstream of the coding sequence and the associated efficient translation signal, and at the appropriate distance upstream of same of the coding sequence to be expressed in a prokaryotic and/or a eukaryotic host cell. It is further preferred that there be a translation termination codon (TAA, TGA, TAG, preferably TAA) upstream of the ribosome binding site-spacer-ACC region of the vector positioned immediately upstream of the translation start site of a coding sequence of interest or of the vector into which such a coding sequence has not yet been inserted. That translation termination codon should be within about 1 to about 100, preferably within about 1 to 30 bases upstream of the ribosome binding site.

Specifically exemplified UTE sequences which give good translation of downstream coding sequences in both eukaryotes and prokaryotes include Ner-ATC (AGGAGGGTTTTTATC, SEQ ID NO:9), LacZ-ACC (AGGAGGCAGACC, SEQ ID NO:7), LacZ-ATC (AGGAGGCAGATC, SEQ ID NO:8) and LacZ.ACC-NcoI-KpnI-AgeI (TAAGGATCCTTAACACAGGAGGCAGACCATGGTACCGGT, SEQ ID NO:10).

The present invention further provides expression cassettes for use in selections, for example, for transformed or transfected cells. Suitable selectable markers include antibiotic resistance genes well known to the art, e.g., the hygromycin resistance gene or the neo gene which confers resistance to kanamycin and neomycin in cells expressing this gene and which confers resistance to suitable antibiotics in eukaryotic as well as in bacterial cells. Similarly, reporter gene cassettes can be prepared using coding sequences of genes suitable for use as reporters with well known and widely accessible coding sequences operably linked to the sequences provided herein which confer the ability to be efficiently translated in both eukaryotes and prokaryotes. Such reporter genes include those encoding chloramphenicol acetyltransferase, luciferase and β-glucuronidase, among others.

BRIEF DESCRIPTION OF THE DRAWINGS

FIG. 2A illustrates the nucleotide sequence of the LacZ.ACC-NcoI-KpnI-AgeI oligonucleotide (SEQ ID NO:10) and restriction endonuclease recognition sites embodied therein. FIG. 2B illustrates the sequence of the LacZ.ACC-NcoI-KpnI-AgeI oligonucleotide with the first three amino acids encoded (SEQ ID NO: 10).

FIG. 3 provides sequence and restriction site information for the LacZ.ACC-AgeI oligonucleotide (SEQ ID NO:11). This is a mutagenic sequence in the 5 prime region of KCR4. The GPI-PLC coding sequence is not included. Unique restriction sites are underlined.

FIG. 4 provides sequence and restriction site information for the LacZ.ACC-NdeI oligonucleotide (SEQ ID NO:12). This is a mutagenic sequence for the 5 prime region of KCR4. The GPI-PLC coding sequence is not included. Unique restriction sites are underlined.

FIG. 5 provides sequence and restriction site information for the LacZ.ACC-NsiI oligonucleotide (SEQ ID NO:13). This is a mutagenic sequence for the 5 prime region of KCR4. The GPI-PLC coding sequence is not included.

FIG. 6 provides sequence and restriction site information for the LacZ-NcoI oligonucleotide (SEQ ID NO:14). This is a mutagenic sequence for the 5 prime region of KCR4. The GPI-PLC coding sequence is not included.

DETAILED DESCRIPTION OF THE INVENTION

Figures 1A, 1B:
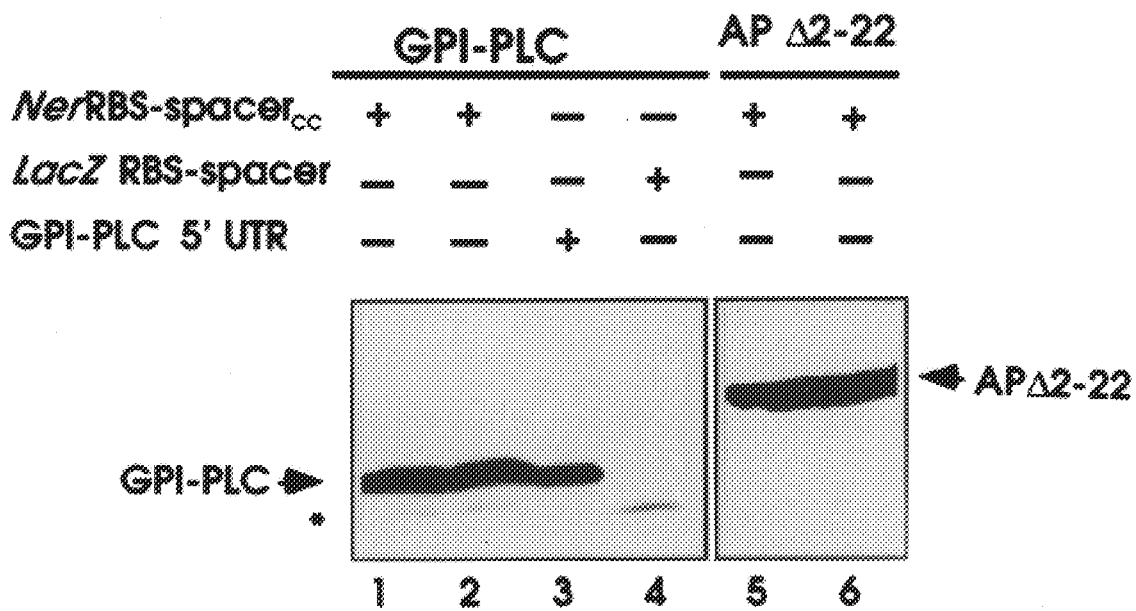
FIG. 1A illustrates the sequences of 5' untranslated regions (UTE sequences) used in the present study. The translation initiation codon is indicated (atg) SEQ ID NOs: 16, 17 and 18 represent the sequences of the Ner RBS-spacer, LacZ RBS-spacer and GPI-PLC 5' UTR (spacer), respectively.
FIG. 1B illustrates the results of in vitro translation using a rabbit reticulocyte lysate (TNT, Promega, Madison, Wis.) with radioactive amino acids and 1 μg of each plasmid tested. The translation products were resolved using SDS-PAGE (10% minigel) and visualized with fluorography as described hereinbelow.

Universal translation enhancement sequence (UTE) is the term used herein to identify nucleotide sequence information which promotes efficient translational expression of a coding sequence of interest in prokaryotic as well as eukaryotic host cells. The minimum sequence is GCC or ACC, and it is positioned immediately upstream of the translational start codon of the coding sequence for which expression is sought. A preferred translation start codon is AUG. This sequence located immediately upstream of the start codon mediates efficient protein synthesis in prokaryotes including but not limited to *Escherichia coli*, and in eukaryotic cells including but not limited to yeast, mammalian cells such as rabbit reticulocytes and *Xenopus laevis*, and protozoans such as Leishmania.

In contrast to the results using the sequences provided herein, it has been previously reported that AGG upstream of the translation start site favors efficient protein synthesis in prokaryotes. The art also teaches that efficient initiation of protein synthesis requires the presence of a consensus sequence (AGGAGG), commonly referred to as the Shine-Delgarno sequence, about 6–13 nucleotides upstream of the translation start site (usually AUG in mRNA).

Novagen (Madison, Wis.) has sold vectors called pCITE (registered trademark of Novagen) which contain the sequence AAT immediately 5' to the translation start site of the coding sequence of interest. There does not appear to be a good match to the consensus Shine-Delgarno sequence for bacterial gene expression in pCITE-4-a-c(+), for example.

Kozak (1987) *J. Mol. Biol.* 196:947–950 has reported that the sequence (GCC)GCCRCCAUGG (SEQ ID NO:15), wherein R is adenine or guanine, is the optimal context for translation of a coding sequence, where the underlined AUG is the translation start site in the mRNA, and that the −3 and +4 positions relative to the translation start site are dominant in determining effects on efficienly of protein synthesis, with further influence from the −6 position.

The present inventors have produced a vector in which there is efficient translation of an inserted coding sequence in both eukaryotic and prokaryotic host cells and using in vitro translation systems. Unless otherwise specified, sequence will be given as the DNA. It is understood in the art that when transcribed into RNA, U is substituted for T. The ribosome binding site and spacer (AGGAGGGTTTTA) (SEQ ID NO:1) of the Ner gene of bacteriophage Mu has been modified to incorporate the nucleotides CC immediately upstream of the translation start site, preferably ATG. The resultant sequence (AGGAGGGTTTTTACC) (SEQ ID NO:2), the Ner-RBS-hybrid spacer$_{CC}$ effects very efficient translation of mRNA in a vertebrate (rabbit reticulocyte lysate) system. By contrast, the control-RBS-spacer from the lacz gene of *Escherichia coli* was ineffective in this cross-species translational stimulation function.

By high fidelity PCR-mediated mutagenesis [Innis et al. (1988) *Proc. Natl. Acad. Sci. USA* 85:9436–9440] the Ner-RBS-hybrid spacer$_{CC}$ was linked to the 5' region of two test coding sequences, *E. coli* alkaline phosphatase [Derman et al. (1993) *EMBO Journal* 12:870–999] and *Trypanosoma brucei* glycosyl phosphatidylinositol phospholipase (GPI-PLC) [Mensa-Wilmot et al. (1995) *Meth. Enzymol.* 250:641–655].

Transcripts from the GPI-PLC constructs which contained the Ner-hybrid spacer$_{CC}$ were robustly translated by rabbit reticulocyte lysates (See FIG. 1B, lanes 1 and 2, representing two independent clones with this construct). Translation in the rabbit reticulocyte lysate for this engineered construct was as efficient as the translation observed from the construct with the native upstream untranslated region (FIG. 1B, lane 3). More importantly, translation initiated from the correct AUG codon, because a 39 kDa was produced. A protein identical in size was produced when a cDNA encoding GPI-PLC was transcribed with the identical RNA polymerase and translated in the rabbit reticulocyte lysate system (See FIG. 1B, compare lanes 1 and 2 with lane 3). To test the possibility that downstream coding sequences might be influencing the translation of the GPI-PLC mRNA from the Ner-hybrid spacer$_{CC}$ plasmids, the coding sequence of the *E. coli* alkaline phosphatase Δ2–22, which has no protein sequence similarity with GPI-PLC, was placed downstream of the Ner-hybrid spacer$_{CC}$. This alkaline phosphatase construct was translated very efficiently to produce the expected 47 kDa protein (FIG. 1B, lanes 5, 6, two representative clones), indicting that the Ner-hybrid spacer$_{CC}$ was solely responsible for the efficient translation of coding sequences positioned immediately downstream of it.

By contrast, transcripts from the GPI-PLC clones which had a lacZ spacer were inefficiently translated in the rabbit reticulocyte lysate as compared with those constructs in which the GPI-PLC was operably linked to the Ner-hybrid spacer$_{CC}$ (compare FIG. 1B, lane 4 with lanes 1 and 2). The full-length GPI-PLC product was not detectable, and what little translation occurred appeared to have initiated predominantly from an internal AUG, generating a truncated protein of 34 kDa (asterisk, FIG. 1B). Incidentally, the GPI-PLC coding sequence linked to the lacZ-RBS-spacer was previously used to express full-length, enzymatically active GPI-PLC in *E. coli* BL21 (DE3) from the T7 promoter [Mensa-Wilmot et al. (1995) supra]. Hence, the coding sequence and the translational control elements in this construct are functional in *E. coli* but not in the eukaryotic model system (rabbit reticulocyte lysate).

Together, these data demonstrate the Ner-hybrid spacer$_{CC}$ is recognized efficiently by eukaryotic ribosomes. Thus, this RBS-spacer combination functions across species lines. The availability of a bifunctional 5'UTR circumvents the need for the usual requirement of separate translational control elements when one wishes to express a protein both in a prokaryotic organism such as *E. coli* and in a mammalian system as well. It is surprising that the Ner-hybrid spacer$_{CC}$ which promotes efficient translational expression in *E. coli* also directs robust translation by mammalian ribosomes as well. The ACC immediately upstream of the translation start site has been associated with enhanced translation in eukaryotic systems [Kozak, M. (1987) *J. Mol. Biol.* 196:947–950], and the present inventors have shown that it surprisingly enhances translation across the prokaryote-eukaryote boundary.

The ability to stably transfect Leishmania with exogenous DNA [LeBowitz et al. (1990) *Proc. Natl. Acad. Sci. USA* 87:9736–9740; Kapler et al. (1990) *Mol. Cell. Biol.* 10:1084–1094; Laban et al. (1990) *Nature* 3:572–574; Laban and Wirth (1989) *Proc. Natl. Acad. Sci. USA* 87:9119–9123] allows testing of the requirement for translation in this protozoan parasite. A 5' untranslated region (5'UTR), using Ner-ACC, which enables efficient translation of proteins in *E. coli* as well as in mammalian expression systems [al-Qahtani and Mensa-Wilmot (1996) *Nucl. Acids. Res.* 24:1173–1174]. Since no reports on sequence requirements for efficient translation in Leishmania are available, we have explored this question in this kinetoplastid. The modified Ner spacer region, Ner-ACC, was placed upstream of a GPI-PLC cDNA in the expression vector pX63NEO [LeBowitz et al. (1993) *Genes Dev.* 7:996–1007] creating plasmid pX.Ner-ACC-GPI-PLC. Leishmania major was transfected and cells were selected using G418. When cells are stabilized by growing in 400 μg/ml of G418, they were tested for GPI-PLC activity. The quantity of GPI-PLC produced was 83,000 units per $10^9$ cells, and the specific activity was 36,000 units per mg of protein.

In a control experiment, Leishmania cells were transfected with plasmid PX.PLCUTR-GTA, which contains the wild type GPI-PLC 5'UTR from *T. brucei*. This plasmid was previously used to express GPI-PLC in Leishmania [Mensa-Wilmot et al. (1994) *J. Cell Biol.* 124:935–947]. The quantity of GPI-PLC produced in these transfectants was 300 U per $10^9$ cells, and the specific activity was 213 units per mg of protein.

In a control experiment we used a plasmid in which the GPI-PLC gene was preceded by the lacZ ribosome binding site-spacer of *E. coli* [Mensa-Wilmot and Englund (1992) *Mol. Biochem. Parasitol.* 56:311–321], the resulting plasmid is termed pX.LacZ-CTA-GPI-PLC. Leishmania transfected with this construct had no GPI-PLC activity. Nevertheless, this lacZ 5'UTR had been successfully used to express GPI-PLC in *E. coli* [Mensa-Wilmot and Englund (1992) supra].

We examined whether it was possible to change the sequence of LacZ-CTA in order to make it functional in Leishmania. We changed the CTA proximal to the initiator ATG of pX.LacZ-CTA-GPI-PLC to ACC, keeping the rest of the sequence the same. This construct (pX.LacZ-ACC-GPI-PLC) was then tested for expression of GPI-PLC activity in Leishmania. This change was enough to promote efficient translation of GPI-PLC in Leishmania (Table 2). The GPI-PLC activity obtained was 81,000 units per $10^9$ cells, and the specific activity was 40,000 units per mg of protein.

We also examined the effect of the sequence GCC at positions −1 to −3 on the expression of GPI-PLC in *L. major*. GCC supports efficient translation in rabbit reticulocyte lysate [Kozak (1994) *Biochimie* 76:815–821]. GPI-PLC activity detected in cells harboring plasmid pX.LacZ-GCC-GPI-PLC was 33,400 units per $10^9$ cells, and the specific activity was 25,000 units, per mg of protein.

Whereas pX.LacZ-CTA-GPI-PLC had no activity in *L. major*, pX.LacZ-ACCGPI-PLC produced large quantities of GPI-PLC (see above); the only difference between these two plasmids is the sequence at −1 to −3 (see Table 1). Therefore, we examined the overall contribution of each nucleotide at positions −1 to −3 by making single nucleotide substitutions from the non-functional 5'UTR (pX.LacZ-CTA-GPI-PLC) into the functional one (pX.LacZ-ACC-GPI-PLC). We replaced each nucleotide in the functional ACC sequence of plasmid pX.LacZ-ACC-GPI-PLC with the corresponding nucleotide from the non-functional CTA sequence. The following plasmids were constructed: pX.LacZ-CCC-GPI-PLC, the A at −3 of pX.LaCZ-ACC-GPI-PLC was changed to a C; pX.LacZ-ATC-GPI-PLC, the C at −2 of pX.LaCZ-ACC-GPI-PLC was changed to a T; and pX.LacZ-ACA-GPI-PLC, the C at −1 was changed to an A. In Leishmania cells harboring pX.LacZ-CCC-GPI-PLC, GPI-PLC produced was produced at a level of 33,100 units per $10^9$ cells, and the specific activity was 15,000 units per mg of protein. Leishmania cells transfected with pX.LacZ-ATC-GPI-PLC produced GPI-PLC activity at 21,100 units per $10^9$ cells, and the specific activity was 9,550 units per mg of protein. Finally, the level of GPI-PLC expressed in Leishmania transfected with pX.LacZ-ACA-GPI-PLC was 40,200 units per $10^9$ cells, and the specific activity was 13,000 units per mg of protein.

To compare the information obtained in the Leishmania system with that obtained in a mammalian expression system, the constructs were transcribed/translated in a rabbit reticulocyte lysate. DNAs containing the different 5'UTE's upstream of the GPI-PLC gene (described above) were cloned into pBluescript II SK, transcribed with T7 RNA polymerase, and translated in the rabbit reticulocyte lysate, thus, allowing a direct comparison and to examine similarities and differences between translation requirements in Leishmania in vivo with mammalian system in vitro.

All of these GPI-PLC constructs were translated (FIG. 1A and 1B). GPI-PLC was efficiently translated when the coding region was preceded by either the Ner-ACC 5'UTE [al-Qahtani and Mensa-Wilmot (1996) supra] (FIG. 1B, lanes 1and 2), or the wild type GPI-PLC 5'UTR from *T. brucei* (FIG. 1B, lane 3). However, the level of expression was reduced when the LacZ ribosome-binding spacer sequence and its variants were used. For instance, when the unmodified LacZ ribosome-binding spacer sequence (pBSK.LacZ-CTA-GPI-PLC) was used, the quantity of GPI-PLC produced was 12% of that obtained with the wild type GPI-PLC 5'UTR from *T. brucei*. The quantity of GPI-PLC expressed using pBSK.LacZ-ACC-GPI-PLC, ACC sequence is at −1 to −3 relative to the initiation codon, was 36% of the quantity obtained with the GPI-PLC 5'UTR from *T. brucei* (plasmid pDH4). Also, when plasmid pBSK.LacZ-CCC-GPI-PLC was used in an in vitro translation reaction, the quantity of GPI-PLC produced was 36% of that obtained using pDH4. The quantity of GPI-PLC produced using plasmid pBSK-LacZ-CCC-GPI-PLC was 18% of the quantity obtained using pDH4. The level of GPI-PLC produced using pBSK.LacZ-ATC-GPI-PLC or pBSK.LacZ-ACA-GPI-PLC were 39% and 43%, respectively, compared with that obtained with the wild-type GPI-PLC 5'UTR from *T. brucei*. Quantitation of translation products is shown in Tables 2 and 4.

These results showed that the wild-type 5'UTE from GPI-PLC and Ner-ACC 5'UTR are the most efficient in supporting translation of GPI-PLC in the rabbit reticulocyte lysate system.

Vectors tailored for gene expression in both eukaryotes and prokaryotes can be improved by the incorporation of one of the UTE sequences of the present invention, e.g., SEQ ID NO:7, SEQ ID NO:8, SEQ ID NO:9, SEQ ID NO:10, SEQ ID NO:11, SEQ ID NO:12, SEQ ID NO:13 and SEQ ID NO:14 downstream of a bifunctional promoter (functional in eukaryotes and prokaryotes) or downstream of dual promoters (promoters separately functional in eukaryotes and prokaryotes. The UTE sequence is located immediately 5' to the translation start site of a coding sequence of interest. SEQ ID NO:10 can supply an ATG translation start signal. Such an expression vector for eukaryotes and prokaryotes can be further modified to include a selectable marker in which the same or a different UTE sequence has been inserted immediately 5' to the translation initiation site of the coding sequence of the antibiotic resistance protein or other selectable marker. Commercially available expression vectors which can be improved in these ways include pCITE vectors (e.g., pCITE-4-a-c(+), U.S. Pat. No. 4,937,190, Novagen, Madison, Wis.), pBK-CMV (Stratagene, La Jolla, Calif.) and pCI-neo (Promega, Madison, Wis.). In pBK-CMV, inserted DNA fragment(s) must provide the ribosome binding site and the ATG for translation initiation as well as the coding sequence to be expressed. The modification of any of the foregoing or of any other vectors is readily within the skill of the art, who can, for example, use ligation of DNA fragments, oligonucleotide site-directed mutagenesis or polymerase chain reaction-mediated mutagenesis.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Ausubel et al. (1994) Current Protocols in *Molecular Biology*, Green Publishing, Inc., and Wiley and Sons, New York, N.Y.; Sambrook et al. (1989) *Molecular Cloning*, Second Edition, Cold Spring Harbor Laboratory, Plainview, New York; Maniatis et al. (1982) *Molecular Cloning*, Cold Spring Harbor Laboratory, Plainview, New York; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101;

Grossman and Moldave (eds.) *Meth. Enzymol.* 65; Miller (ed.) (1972) *Experiments in Molecular Genetics*, Cold Spring Harbor Laboratory, Cold Spring Harbor, New York; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein. All references cited in the present application are incorporated by reference herein.

The following examples are provided for illustrative purposes, and are not intended to limit the scope of the invention as claimed herein. Any variations in the exemplified sequences and methods which occur to the skilled artisan are intended to fall within the scope of the present invention.

EXAMPLES

Example 1. Ner-hybrid-spacer$_{CC}$

A RBS and spacer from the Ner gene of bacteriophage Mu (AGGAGGGTTTTA; SEQ ID NO:1) has been used previously for high level protein expression in the prokaryotes *E. coli* and Streptomyces [Buell et al. (1985) *Nucl. Acids Res.* 13:1923–1938; Gray et al. (1984) *Gene* 32:21–30]. The sequence of this RBS-spacer sequence was altered to add CC at its 3' end to give SEQ ID NO:2 (AGGAGGGTTTTTACC).

By high fidelity polymerase chain reaction-mediated mutagenesis the Ner-hybrid spacer$_{CC}$ was linked to the 5' regions of two test coding sequences, alkaline phosphatase of *E. coli*, and glycerol phosphatidylinositol phospholipase of *T. brucei* [Hereld et al. (1988) *Proc. Natl. Acad. Sci. USA* 85:8914–8918]. Primers and templates were as follows: alkaline phosphatase Δ2–22: template, pAD135 [Derman et al. (1993) *EMBO Journal* 12:879–888]; 5' primer (F1 APΔ2–22, TAAGGATCCTTAACTTAGGAGGGTTTTTACCATG ACACCAGAAATGCCTGTTCTGG, SEQ ID NO:3); reverse primer (R446-BG2-AP, GATCGGATCCTTAAGATCTGCCCCAGAGCGGCTTT-CATGG, SEQ ID NO:4). For GPI-PLC mutagenesis, the template was pDH4 [Hereld et al. 1988) supra]; the 5' primer was KCR10 (TAAGGATCCTTAACACAGGAGGGTTTTTACCATG TTTGGTGGT, SEQ ID NO:5) and the reverse primer was KCR5 (TATGTGGATCCTTATGACCTTGCGGTTT-GGTT, SEQ ID NO:6). All PCR primers contained a BamHI site for subcloning purposes. PCR products were digested with BamHI and cloned into pBluescriptII(SK) (+) (Stratagene, La Jolla, Calif.) under the transcriptional regulation of the phage T7 promoter system therein. A GPI-PLC plasmid (pKMW2) [Mensa-Wilmot et al. (1995) supra] containing the RBS (AGGAGG) and spacer (CAGCTA) from the *E,. coli* lacZ gene was used as a control for the in vitro translation experiments. All other sequences in the primers were identical to those used in the construction of the Ner spacer clone. Identical amounts of plasmids purified by anion exchange chromatography (Qiagen tip-20; Qiagen, Chatsworth, Calif.) were transcribed with purified T7 polymerase and translated in the same reaction mixture using rabbit reticulocyte lysate (TNT T7 coupled transcription/translation system; Promega, Madison, Wis.) containing [$^{35}$S]-methionine as directed by the manufacturer. Translation products were resolved by sodium dodecyl sulfate-polyacrylamide gel electrophoresis (10% gels) and detected by fluorography (Hyperfilm; Amersham, 20 hrs, –70° C.).

To assess the efficiency of translation of the GPI-PLC construct containing the Ner-hybrid-spacer$_{CC}$, the quantity of product was compared with that produced from a GPI-PLC cDNA clone with the authentic eukaryotic 5' UTE pDH4 [Hereld et al. (1988) supra]. Because the cDNA was cloned downstream of the T7 promoter in pBluescript (Stratagene, La Jolla, Calif.), identical reagents could be used for analysis of constructs with the *E. coli* 5' UTEs could be used for the experiments involving expression of the cDNA. The nine bases preceding the initiator ATG in this cDNA are ATCATTGTA.

While the Ner$_{ACC}$-GPI-PLC construct gave efficient translation in the two eukaryotic systems tested but relatively poor expression in an *E. coli* host, a LacZ$_{ACC}$-GPI-PLC construct gave dramatically higher levels of expression for the test coding sequence in all three test systems. In these experiments the vector and coding sequences were as described above and in al-Qahtani and Mensa Wilmot (1996) *Nucl. Acids Res.* 24:1173–1174. Comparative results are summarized in Table 2.

The LacZAcc sequence immediately upstream of the translation start codon (ATG) of the GPI-PLC reporter gene was varied by oligonucleotide mutagenesis using polymerase chain reaction methods, and expression levels were monitored. Table 3 presents the results of GPI-PLC expression downstream of varied LacZ sequences immediately upstream of the ATG translation start codon in the *E. coli* host system. Table 4 presents the results for five LacZ variants and two Ner variants as tested in the rabbit reticulocyte test system. Expression levels are expressed relative to the Ner-ACC sequence. Table 3 presents specific activities in *E. coli* for Ner-ACC, Ner-ATC and various LacZ variants.

The efficiency of translation was tested in vivo in *Leishmania major* cells using a GPI-PLC construct in which the translation start codon was preceded by ACC or CTA. The ACC construct gave about 170-fold higher protein expression than the construct with CTA immediate upstream of the translation start site.

Example 2. Variations of the Ner-hybrid-spacer$_{CC}$

High fidelity PCR-mediated mutagenesis was used to vary the sequence immediately 5' to the ATG translation initiation codon. Efficiency of translation was measured using SDS-PAGE and fluorography of the products. Table 1 provides the results for this experiments, with relative amounts of translation products in a rabbit reticulocyte assay.

TABLE 1

Relative translation efficiency for variations of Ner-hybrid-spacer$_{cc}$

| Sequence 5' to AUG | Relative level of translation |
|---|---|
| ACC | ++++ |
| GCC | ++ |
| CCC | + |
| ATC | ++ |
| ACA | ++ |
| TTA | + |
| CTA | – |

Construction of Plasmids used in this study: Different 5'UTEs were introduced upstream of GPI-PLC coding sequence by polymerase chain reaction (PCR)-based mutagenesis [al-Qahtani and Mensa-Wilmot (1996) supra]. The desired UTE was included in the sense primer (Table 1) used to amplify GPI-PLC gene. Each of the sense primers have the following features, a BamHI site followed by the 5' UTE of interest and the sequence encoding the first 7 amino acids (residues 1 to 7) of GPI-PLC. It also includes an in-frame stop codon to stop synthesis of any upstream proteins [Mensa-Wilmot and Englund (1992) Nucl. Acids Res. 20:143], The reverse primer (KCR5) contains a BamHI site, a stop codon and the complementary sequence encoding the last 7 amino acids (residues 352–358) of GPI-PLC (Table 1).

High fidelity PCR [Innis et al. (1988) Proc. Natl. Acad. Sci. USA 85:3436–3440] was performed in a 100 µl reaction in 10 mM Tris-HCl pH 8, 50 mM KCl), 2.5 mM MgCl, 0.05% Tween 20 (Fisher Scientific), 0.05% Nonidet-P 40 (NP-40) (Calbiochem, San Diego, Calif.), final concentration (2.5 mm MgCl, 0.05% Tween 20 (Fisher Scientific), 0.05% nonidet-P40 (NP-40) (Calbiochem), 10 mm Tris-HCl pH 8, 50 mM KCl). The reaction contained a sense primer of interest (0.5 µM, final concentration), KCR5 (the reverse primer, 0.5 µM, final concentration), plasmid pKMW2 [Mensa-Wilmot and Englund (1992) supra] (30 ng) as a template, deoxynucleotides triphosphate (dNTP's) (0.250 mM, final concentration of each nucleotide), and 5 U of Taq polymerase (Fischer Scientific). The PCR reaction was performed for 25 cycles. Each cycle consisted of 1 min at 95° C., 1.5 min at 56° C., and 2 min at 74° C. At the end of the 25th cycle, an 8 minute extension at 74° C. was performed. The PCR product was purified by ultrafiltration using microcon-100 (Amicon, Beverly, Mass.). The PCR product was digested with BamHI for 3 hours at 37° C. followed by treatment with phenol/chloroform/isoamylalcohol (25/24/1) and ethanol precipitation. The BamHl-digested product was then ligated to pX63NEO [LeBowitz et al. (1993) supra] that had been digested with BamHI and treated with alkaline phosphatase. The ligation reaction was performed at 14° C. overnight, and the ligation product was transformed into E. coli (DH5a) cells. Colonies were screened by PCR using same primers used for the initial PCR reaction. The orientation of the insert was determined using a sense (forward) primer specific for the neomycin phosphotransferase-coding region in combination with KCR5. In pX63NEO, the gene encoding neomycin phosphotransferase is located upstream of the BamHI site that was used for cloning GPI-PLC CDNA fragments.

Transfection of Leishmania cells: Plasmid prepared by Anion exchange chromatography (Qiagen tip-100, Qiagen, Chatsworth, Calif.) was transfected into Leishmania major HOM/IQ/73/LCR-L32 strain. Cells grown to late log phase were collected by centrifugation (1,000×g in Sorval RT6000 (Du Pont), washed in electroporation buffer (21 mM HEPES pH 7.5, 137 mM NaCl, 5 mM KCl, 0.7 mM $Na_2PO_4$, 6 mM glucose) and pelleted. Cells were resuspended in electroporation buffer at $5 \times 10^8$ cells/ml DNA (50 µg) in distilled water was mixed with $10^8$ cells and subjected to electroporation immediately. Electroporation conditions were two rounds of application of a voltage of 2.25 kV/cm with capacitance of 500 µF. Cells were immediately stored on ice, and after 15 minutes transferred to 10 ml M199 medium (supplemented with 10% fetal bovine serum, 40 mM HEPES pH 7.4, 0.1 µM adenine, 0.05% hemin, and 0.0001% biotin) in 25 ml canted-neck flasks (Corning, Corning, N.Y.). Following 48-hour incubation at 26° C., G418 was added at 50 µg/ml for selection. After stepwise increase of drug concentration, parasites adapted to grow at 400 µg/ml of G418 were used for GPI-PLC assays.

Cell lysis, fractionation, and GPI-PLC assay: Cells ($2 \times 10^8$) were lysed in 1 ml of hypotonic buffer (10 mM Tris-HCl pH 8, 1 MM EDTA) supplemented with protease inhibitor cocktail (phosphoramidon, leupeptin, aprotinin, antipain, EDTA, and (4-amid-inophenyl)-methane sulfonyl fluoride (APMSF) (Boehringer Mannheim, Indianapolis, Ind.)). Following incubation on ice for 1 hour, the lysate was centrifuged for 30 min at 16,500×g in a microfuge (Marathon 16 KM, Fisher Scientific). The supernatant was discarded and the pellet (membrane fraction (MF)) was resuspended in 100 µl of 1X assay buffer (AB) (1% NP-40, 5 mM EDTA, 50 mM Tris-HCl pH 8).

GPI-PLC was assayed using [$^3$H]myristate-labeled mfVSG as a substrate [Mensa-Wilmot et al. (1995) supra]. A typical reaction includes in 30 µl of 1×AB, 2 µg [$^3$H] mfVSG (7,000 dpm) and 2 µl lysate of MF assembled on ice in a 1.5 ml microfuge tube. For quantitative GPI-PLC assays, MF was diluted between 10 to 400-fold in 1X AB to obtain values within the linear range of the assay (0.1–1 U) [Mensa-Wilmot et al. (1995) Meth. Enzymol. 250:641–655]. Tubes containing the reaction components are incubated at 37° C. for 30 minutes and the reaction is stopped by addition of 500 µl of water-saturated n-butanol and vortexing at room temperature. Butanol soluble material ([$^3$H] dimyristoylglycerol) (400 µl) was counted in a liquid scintillation counter (Beckman LS6000 TA) after the addition of counting fluid.

In vitro translation; A microgram of plasmid DNA, purified by anion exchange chromatography (Qiagen tip-20, Qiagen) was translated in a coupled transcription-translation system using rabbit reticulocyte lysate (Promega, Madison, Wis.), as directed by the manufacturer. A typical 30 µl translation reaction contains 15 µl of rabbit reticulocyte lysate, 1 µl of 1 mM amino acids (minus methionine), 1 µl RNA polymerase, 1 µl ribonuclease inhibitor (RNAsin, 100 U/µl) and 4 µL [$^{35}$S]methionine (1000 mCi/mmol (Amersham).

Example 3. LacZ.ACC-NcoI-KpnI-AgeI Constructs

FIG. 2A illustrates the nucleotide sequence of the LacZ.ACC-NcoI-KpnI-AgeI oligonucleotide (SEQ ID NO:10) and restriction endonuclease recognition sites embodied therein. This sequence can be inserted into a vector with a dual promoter, i.e., one functional replication and expression both in eukaryotic host cells and in prokaryotic host cells, e.g., E. coli, to give vectors which direct the efficient expression of a downstream coding sequence in both eukaryotic and prokaryotic recombinant host cells. The LacZ.ACC-NcoI-KpnI-AgeI sequence is improved over the NerAcc sequence. Either of these sequences can be used to modify commercially available vectors including, without limitation, pci-neo (Promega, Madison, Wis.) and PBK-CMV (Stratagene, La Jolla, Calif.). Vectors can be modified to include a sequence of the present invention adjacent to the translation start sites of a coding sequence of interest and/or a selectable marker and/or a reporter gene which serves to indicate the successful transformation of a (recombinant) host cell.

Example 4. Other Sequence Modifications

Additional sequences suitable for modifying vectors for improved expression and/or convenience of cloning include those sequences described in FIGS. 3–6.FIG. 3 provides sequence and restriction site information for LacZ.ACC-AgeI; FIG. 4 provides sequence and restriction site information for LacZ.ACC-NdeI; FIG. 5 provides sequence and restriction site information for LacZ.ACC-NsiI; and FIG. 6 provides sequence and restriction site information for LacZ-NcoI. Each of these oligonucleotides can be used to modify the region immediately upstream of the coding sequence in a suitable vector.

TABLE 2

Relative Activity of 5' UTRs in
Leishmania, Rabbit Reticulocyte and *E. coli*

| System | Ner-ACC | LacZ-ACC | LacZ-ATC | LacZ-CTA |
|---|---|---|---|---|
| Leishmania | 0.90 | 1.00 | 0.24 | 0.00 |
| Rabbit Reticuloayte | 1.00 | 0.49 | 0.48 | 0.20 |
| *E. coli* | 0.003 | 0.51 | 1.00 | 0.78 |
| Relative Utility Index | 0.003 | 0.25 | 0.12 | 0.00 |

Relative Utility Index was calaulated as the produat of the relative efficiencies (i.e. in comparison to the best performing construct) in the 3 expression systems.

TABLE 3

GPI-PLC Specific Activity (U/mg) in *E. coli*

| Mutant | U/mg | U/mg |
|---|---|---|
| Ner-ACC | 100 | |
| Ner-ATC | | 20,500 |
| LacZ-CTA | 26,700 | |
| LacZ-ACC | 17,500 | |
| LacZ-GCC | 18,000 | |
| LacZ-CCC | 13,200 | |

TABLE 3-continued

GPI-PLC Specific Activity (U/mg) in *E. coli*

| Mutant | U/mg | U/mg |
|---|---|---|
| LacZ-ATC | 34,400 | 58,000 |
| LacZ-ACA | 18,100 | |
| LacZ-CCA | | 40,000 |
| LacZ-TTA | | 5,000 |
| LacZ-CAT | | 41,000 |
| LacZ-CTC | | 9 |

TABLE 4

GPI-PLC Expression in Rabbit Reticulocyte System

| Clone | Rel. Act. |
|---|---|
| Ner-ACC | 1.00 |
| Ner-ATC | 0.50 |
| LacZ-ACC | 0.48 |
| LacZ-CTC | 0.27 |
| LacZ-CCA | 0.36 |
| LacZ-TTA | 0.20 |
| LacZ-CAT | 0.12 |

We claim:

1. A method for efficient expression of a recombinant protein in a prokaryotic host cell or in a recombinant eukatyotic cell, said method comprising the steps of;
   (a) operably linking a DNA fragment encoding said protein with at least one promoter functional in both eukaryotic and said prokaryotic host cells to produce an expression cassette, wherein said expression cassette comprises a nucleotide sequence ATC immediately upstream of a translation start site;
   (b) incorporating said expression cassette in a vector that replicates and is maintained within both eukaryotic and prokaryotic host cells to produce an expression vector;
   (c) transforming or transfecting said expression vector into a prokaryotic or eukaryotic host cell to produce a recombinant host cell, and
   (d) culturing said recombinant host cell under conditions that result in expression of the protein encoded within said expression cassette.

2. A vector that expresses a desired coding sequence in both a eukaryote and a prokaryote, said vector comprising an upstream translation enhancing sequence selected from the group consisting of SEQ ID NO:2, SEQ ID NO:7, SEQ ID NO:8, SEQ ID NO:9, SEQ ID NO:10, SEQ ID NO:11, SEQ ID NO:12, SEQ ID NO:13 and SEQ ID NO:14 positioned immediately upstream of a translation initiation codon of said coding sequence.

3. The vector of claim 2 wherein said coding sequence of interest is a selectable marker.

4. The vector of claim 3 wherein said selectable marker determines kanamycin resistance or hygromycin resistance.

5. A recombinant host cell comprising the expression vector of claim 2.

6. A method for efficient expression of a recombinant protein in a prokaryotic host cell or in a recombinant eukaryotic cell, said method comprising the steps of:
   (a) operably lining a DNA fragment encoding said protein with at least one promoter functional in said eukaryotic and said prokaryotic host cells to produce an expression cassette wherein said expression cassette comprises a nucleotide sequence selected from the group consisting SEQ ID NO:2, SEQ ID NO:7, SEQ ID NO:8, SEQ ID NO:9, SEQ ID NO:10, SEQ ID NO:11, SEQ ID NO:12, SEQ ID NO:13 and SEQ ID NO:14 of immediately upstream of a translation start site;
   (b) incorporating said expression cassette in a vector that replicates and is maintained within said eukaryotic and said prokaryotic host cells to produce an expression vector;
   (c) transforming or transfecting said expression vector into a prokaryotic or eukaryotic host cell to produce a recombinant host cell, and
   (d) culturing said recombinant host cell under conditions that result in expression of the protein encoded within said expression cassette.

* * * * *

UNITED STATES PATENT AND TRADEMARK OFFICE
CERTIFICATE OF CORRECTION

PATENT NO. : 5,874,242     Page 1 of 2

DATED : February 23, 1999

INVENTOR(S) : Mensa-Wilmot

It is certified that error appears in the above-identified patent and that said Letters Patent is hereby corrected as shown below:

On the title page, Item [56],

In the References Cited:

In the Margolskee et al. reference, line 1, replace "shittle" with --shuttle--; and replace "stabe" with --stable--.

In the LeBowitz et al. reference, line 1, replace "poly(a)" with --poly(A)--.

In the Figures:

In Fig. 3, top strand of the nucleotide sequence, replace nucleotide 28 "G" with --C--

In Col. 3, line 16, underline nucleotides 10, 11 and 12; i.e. --AUG--.

In Col. 5, line 29, rewrite "ACCGPI" as --ACC-GPI--.

UNITED STATES PATENT AND TRADEMARK OFFICE
CERTIFICATE OF CORRECTION

PATENT NO. : 5,874,242

DATED : February 23, 1999

INVENTOR(S) : Mensa-Wilmot

It is certified that error appears in the above-identified patent and that said Letters Patent is hereby corrected as shown below:

In Col. 7, line 58, rewrite "*E., coli*" as --*E. coli*--.

In Col. 9, line 5, between "primer" and "(Table 1)", insert --(KCR4)--.

In Col. 9, line 14, delete "(Table 1)".

In Col. 9, lines 17 and 19, replace "MgCl" with --$MgCl_2$--.

In Col. 9, line 45, rewrite "CDNA" as --cDNA--.

In Col. 9, line 52, replace "$Na_2PO_4$" with --$Na_2HPO_4$--.

In Col. 10, line 1, rewrite "MM EDTA" as --mM EDTA--.

In Col. 11, Table 2, line 17, replace "calaulated" with --calculated--; and "produat" with --product--.

Signed and Sealed this

Sixth Day of July, 1999

Q. TODD DICKINSON

Attest:

*Attesting Officer*　　　　　*Acting Commissioner of Patents and Trademarks*